United States Patent [19]

Mackles et al.

[11] Patent Number: 5,294,447
[45] Date of Patent: Mar. 15, 1994

[54] ANHYDROUS TOPICAL COMPOSITIONS WHICH DRY RAPIDLY ON CONTACT

[76] Inventors: Leonard Mackles, 311 E. 23rd St., New York, N.Y. 10010; Leonard Chavkin, R.R. 1, Box 90, Bloomsbury, N.J. 08804

[21] Appl. No.: 933,788

[22] Filed: Aug. 24, 1992

Related U.S. Application Data

[62] Division of Ser. No. 684,246, Apr. 12, 1991, Pat. No. 5,178,881.

[51] Int. Cl.$^5$ ................................................ A61K 9/14
[52] U.S. Cl. ..................................... 424/489; 424/66; 424/68
[58] Field of Search ..................... 424/489, 66, 68; 514/770

[56] References Cited

U.S. PATENT DOCUMENTS

| | | | |
|---|---|---|---|
| 4,526,780 | 7/1985 | Marschner et al. | 514/770 |
| 4,863,721 | 9/1989 | Beck et al. | 424/66 |
| 4,937,069 | 6/1990 | Shin | 424/68 |
| 5,137,714 | 8/1992 | Scott | 514/785 |

*Primary Examiner*—Thurman K. Page
*Assistant Examiner*—William E. Benston, Jr.
*Attorney, Agent, or Firm*—Omri M. Behr; Matthew J. McDonald

[57] ABSTRACT

A substantially anhydrous composition suitable for topical application which contain 10–80% by weight of an anhydrous base which is liquid or semi-solid at room temperature; and 5–50% by weight of polyolefin microspherical particles having an average diameter of less than 25 microns, the amount of microspherical particles constituting at least 30% by weight of the anhydrous base.

5 Claims, No Drawings

ANHYDROUS TOPICAL COMPOSITIONS WHICH DRY RAPIDLY ON CONTACT

This application is a division of application Ser. No. 07/684,246, filed Apr. 12, 1991, now U.S. Pat. No. 5,178,881.

FIELD OF THE INVENTION

This invention concerns anhydrous compositions for topical application which dry quickly after application, have substantially no greasy or oily feel and have good retention even when the skin is moistened.

BACKGROUND OF THE INVENTION

There are many products intended for application to the skin for therapeutic or cosmetic purposes that are best formulated as anhydrous systems. Anhydrous liquids or semi-solids were the original topical ointment and lotion vehicles. Mineral oil and petrolatum are examples, as are the animal and vegetable fats and oils, of the bases used as dermatological vehicles or cosmetic carriers. Pharmaceutical formularies include ointments, creams and lotions, containing examples of anhydrous dermatological vehicles for topical application to the skin.

Although these anhydrous topical bases were excellent delivery systems for medications and were proven to be the best skin protective and moisturizing agents, their use is limited by the fact that consumers reject them on the basis of their greasy feel. This essential negative has limited their application to products for serious therapeutic and cosmetic uses, where their greasiness is tolerated.

There have been several attempts to make dermatological vehicles more aesthetically acceptable. In one such attempt clays, starches, polysaccharides or cellulosics have been used to replace the oils in anhydrous systems in order to dry them out. These substitutions have generally been without success. While the substitute materials can be used in small amounts they are usually not successful unless used in large amounts, where these particular materials cause the products to become pasty and sticky and to cause agglomeration of settling materials or clogging in aerosols.

In a further effort to improve dermatological vehicles, water soluble and water dispersible (washable) systems were developed. The majority of these were oil-in-water emulsion systems in which the oil was dispersed in at least 50% water to form a lotion or a cream. These creams spread easily on the skin, were rubbed in, or were absorbed rapidly with reduced greasiness or stickiness and are much more cosmetically elegant and acceptable to consumers.

Although these systems have thus been considered superior to anhydrous topical bases, they suffer from some negatives as compared to the original anhydrous systems.

Newer washable systems are more easily removed so their action is fleeting.

They are perceived as wet and cold feeling during application and require time for rub-in or absorption to feel dry.

The emulsifier in these systems used are sometimes irritating to the skin.

The protective, emollient or moisturizing effect of the washable systems is very significantly less than the anhydrous systems.

Water sometimes results in active ingredient instability; as with antibiotics.

Water presents microbiological problems requiring the use of preservatives.

Emulsions are inherently unstable systems that separate in time.

SUMMARY OF THE INVENTION

We have discovered a novel way to achieve the elegance of a cosmetic compositions cream without the use of water or emulsion systems. We have found that the incorporation of polyolefin microspherical particles (PMP) into anhydrous compositions will render these compositions cosmetically elegant. Greasiness or stickiness is eliminated: absorption to a dry feel is rapid, and a smooth soft feel on the skin is achieved almost instantly.

None of the positive attributes of the oily bases is sacrificed. Since water and emulsifiers are not required, irritation is eliminated, instability of active ingredients is avoided, wetness and slow drying are eliminated.

Moisturizing and skin protection properties are not diminished as in emulsion systems. Preservation problems, even in the absence of preservatives, are absent.

In the application of our invention we have found it possible to modify the application properties of a variety of commonly used anhydrous liquid or semisolid (m.p. below 50° C.) topical agents to achieve a smooth, dry application by the inclusion of at least 30% PMP by weight, of the oils present.

The anhydrous compositions which have the above desirable characteristics of both anhydrous and washable compositions comprise from 10 to 80% anhydrous base and 5 to 50% polyolefin microspherical particles of average diameter less than 25 microns. The amount of polyolefin microspherical particles in the composition is from 30 to 130% by weight of the base. These anhydrous compositions may be in lotion, ointment, solid or aerosol form. In addition to the base and microspherical particles, the anhydrous compositions may contain from 1 to 50% of an active ingredient. Suitable active ingredients for these compositions are antiperspirant, analgesic, sunscreen and insect repellent compounds. The anhydrous compositions of the invention are made by conventional mixing techniques.

DETAILED DESCRIPTION OF THE INVENTION

Anhydrous bases for use in the invention include animal, vegetable and mineral fats or oils or synthetic anhydrous substances, all of which have a melting point of below 50° C. Suitable animal fats include lanolin, lard, fish oils and fish liver oils. Suitable vegetable oils include cotton seed, corn, soybean, canola and castor oil as well as, coconut oil and cocoa butter. Also suitable are mineral oils and petrolatums. Suitable synthetic substances include isopropyl fatty acid esters such as palmitate and myristate; glycerol monolaurate or monooleate; polyglyceryl fatty acid esters; medium chain triglycerides (i.e., C4 to C14); acetylated monoglycerides; propylene glycol; polypropylene oxide polymers and their fatty acid esters; glycerin; polyethylene oxide polymers and their fatty acid esters; isostearyl alcohol, silicone oils and esters such as cyclomethicones; e.g., octamethylcyclotetrasiloxane.

Although the suitable cyclomethicones such as octamethylcyclotetrasiloxane and decamethyl-cyclopentasiloxane are volatile silicones they are not as volatile as ethanol. Therefore, cyclomethicones do not feel cold on the skin when applied thereto and are not perceived to be wet.

In addition to these volatile silicones, other anhydrous "absorbable" oils are suitable as bases in the invention. These include, ethyl phthalate, butyl phthalate, polyoxypropylene 14 butyl ether, polyoxypropylene 15 stearyl ether and other liquid esters and ethers. Although all of these oily materials feel warm and dry upon application, they are perceptibly greasy and oily unless combined in the composition of the invention.

It is understood that one or more of these base materials may be combined in the anhydrous compositions in order to yield a liquid semisolid or solid composition at room temperature. Additionally, different combinations of base substances may be made to produce a liquid composition having a desirable viscosity.

The polyolefin microspherical particles suitable for use in the anhydrous compositions are well known. Among the preferred particles for use in the compositions are those having average diameter of less than 25 microns. One such material is a microfine polyolefin powder produced by U.S.I. Chemicals: "Microthene" is a polyethylene with regular spherical uniform particles of average diameter of less than 20 microns. These particles have a density of 0.915–0.960 grams per cubic centimeter, a melt index of 5-55 (g/10 min.) and a softening point between 75°-128° C. Most preferred of the polyolefin powders is Microthene FN 510.

Because polyolefin microspherical particles form a low density material with small particle size, the particles do not readily settle in liquid systems. Therefore, problems of settling and packing are eliminated.

The polyolefin microspherical particles are suitably incorporated in the anhydrous compositions at from 5 to 50% by weight of the composition and in an amount which is from 30 to 130% by weight of the base material present in the composition. Preferably, the composition may include from 30 to 40% by weight of the polyolefin microspherical particles.

Among the active ingredients suitable for inclusion in the anhydrous compositions are antiperspirant compounds. Suitable such antiperspirant compounds include aluminum chloride, aluminum chlorohydrate, aluminum chlorohydrate-propylene glycol complex, aluminum zirconium tetrachlorohydrate-glycine and aluminum pentachlorohydrate. Many of these antiperspirant compounds are usually found in the form of fine powders. As such, the antiperspirant materials may be suspended in the anhydrous system where they remain relatively inert until they come in contact with moisture from the skin.

The anhydrous compositions may suitably include antiperspirant compound at a level of 5 to 50% by weight of the composition, preferably 10 to 30% by weight of the composition.

Other suitable active ingredients for the anhydrous compositions include insect repellent (e.g., N,N-diethyl toluamide DEET)); sunscreen (octyl dimethyl PABA); and analgesic compounds (e.g., methyl salicylate). The amounts of these active ingredients may also be 1 to 50% by weight of the composition or alternatively, 20 to 30% by weight of the composition.

Optional ingredients for including in the anhydrous compositions include waxes, fragrances, talcs, germicides, color and suspending agents such as fumed silica or treated bentonites.

The anhydrous compositions of the invention may take several forms: liquid, ointment, solid stick or aerosol. In each of these forms the anhydrous composition, when applied, achieves a smooth dry application with no greasy or oily feel.

One embodiment of the anhydrous composition which is a lotion, the base includes mineral oil and lanolin accompanied by the Microthene FN510. Alternatively, the base may be triglyceride or isopropyl myristate.

Where the composition is an ointment embodiment the base may be white petrolatum and where a cream is desired may be mineral oil.

Aerosol embodiments of the anhydrous composition may be made by conventional methods thus, an initial concentrate is made including anhydrous base with polyolefin microspherical particles optionally with active ingredient or other elements. The concentrate is then added to a propellent (e.g. isobutane) and submitted for aerosol filling.

To make the lotion and ointment forms of the anhydrous composition the anhydrous base and polyolefin microspherical particles should be stirred together and subjected to high speed mixing to achieve uniform dispersion. When base materials of melting point above room temperature are being used the base should initially be heated sufficient to render it easily mixable; for example, where the base is decamethyl cyclopentasiloxane and stearyl alcohol, the base material may suitable be heated to 70° C. prior to addition of the polyolefin microspherical particles. This heating renders the mixing step easier and effects suitable dispersion of the microspherical particles more quickly and easily.

Where additional ingredients are included in the composition they should be added step wise with mixing following the addition of each ingredient.

In order to make aerosol forms of the anhydrous compositions, a concentrate should first be made. The concentrate includes the anhydrous base, as well as, polyolefin microspherical particles and other active or optional ingredients. As with lotions, ointments and sticks this concentrate is made by mixing the ingredients step wise into the anhydrous base (liquified by heating if desirable). The mixing of these ingredients into the concentrate is again by high speed mixing to achieve uniform dispersion. Once the concentrate is formed it should be homogenized.

The homogenized concentrate is then combined with sufficient propellant for example, isobutane under pressure and this "aerosol fill" is then subjected to filling in pressurized containers.

For a further understanding of the invention, reference is made to the following examples.

Unless otherwise noted, all percentages in this specification are percentages by weight of the composition.

EXAMPLE 1

An anhydrous hand and skin lotion composition is made comprising 50% mineral oil (USP 200/210 SSU) 5% lanolin (anhydrous) and 45% Microthene FN510. The lotion is made by initially heating the mineral oil and lanolin together to 60° C. Upon reaching this temperature the FN510 is stirred in followed by cooling to room temperature.

The resultant hand and skin lotion rubs in dry almost instantly to give a smooth, silky feel to the skin.

EXAMPLE 2

An anhydrous after bath lotion composition is made comprising 55% isopropyl myristate, 44% Microthene FF510 and 1% Cabosil M-5 (fumed silica). All ingredients are mixed without heating under high speed stirring to achieve uniform dispersion. The resultant after bath lotion rubs into the skin to give a smooth soft feel without oily or greasiness.

EXAMPLE 3

An anhydrous petrolatum ointment is made including 66.7% petrolatum USP, White and 33.3 Microthene FN510. Initially the petrolatum is heated to 50° C. until it is melted, the FN510 microspheres are then stirred in and the combination is subjected to high speed to achieve uniform dispersion. The mixture is then cooled to 55° C. and poured out of the mixing vessel into storage vessels.

This petrolatum ointment rubs into the skin almost immediately leaving a dry and powdery feeling on the surface in contrast to untreated petrolatum which leaves a greasy and messy feeling.

EXAMPLE 4

A topical analgesic ointment is made including 19% methyl salicylate, 15% menthol USP, 25% white petrolatum USP, 40% Microthene FN510 and 1% Cabosil M-5(fumed silica). In making this ointment, the methyl salicylate, menthol and petrolatum are combined in mixing vessel and heated together to 60° C. The microspheres are then added to the liquified mixture and stirred at high speed to achieve uniform dispersion. Afterward the fumed silica is added; the batch is then cooled to room temperature and removed into a storage vessel.

The resultant topical analgesic rubbed into the skin leaving no greasy feel thereon.

EXAMPLE 5

An anhydrous liquid roll-on antiperspirant composition is made from the following:

|  | % |
| --- | --- |
| 1. Decamethyl cyclopentasiloxane (Pentamer) | 38.00 |
| 2. Microthene FN510 | 33.00 |
| 3. Polyoxypropylene 14 butyl ether | 4.00 |
| 4. Aluminum chlorohydrate, ultra fine (ACH) | 25.00 |

The cyclomethicone and the polyoxypropylene 14 butyl ether are mixed with high speed stirring. The ACH is then stirred in followed by the FN510. The batch is mixed until uniform. The batch is homogenized for uniformly and then packaged in roll-on containers.

Other antiperspirant active chemicals may be substituted for the ACH without any noticeable difference.

EXAMPLE 6

An anhydrous antiperspirant cream composition is made from the following:

|  | % |
| --- | --- |
| 1. Decamethyl cyclopentasiloxane (Pentamer) | 39.00 |
| 2. Microthene FN510 | 29.00 |
| 3. Polyoxypropylene 14 butyl ether | 4.00 |
| 4. Aluminum chlorohydrate (ACH) | 25.00 |
| 5. Cabosil M-5 (Fumed Silicon Dioxide) | 3.00 |

Cyclomethicone is mixed in a mixing vessel with the ACH and the polyoxypropylene 14 butyl ether. When this mixture is uniform the microspheres FN510 are added with high speed mixing until the mixture is smooth and uniform. At this point, the fumed silicon dioxide is added to the mixing vessel and high speed mixing until a uniform paste is formed.

The resulting antiperspirant cream ointment delivers a product which feels dry upon application. Other antiperspirant actives may be substituted for ACH without noticeable difference.

EXAMPLE 7

An anhydrous antiperspirant stick composition is made from the following:

|  | % |
| --- | --- |
| 1. Decamethyl cyclopentasiloxane (Pentamer) | 26.00 |
| 2. Microthene FN510 | 35.00 |
| 3. Polyoxypropylene 15 stearyl ether | 4.00 |
| 4. Aluminum chlorohydrate, ultra fine (ACH) | 25.00 |
| 5. Stearyl alcohol | 10.00 |

Ingredients 1, 3 and 5 are heated in a mixing vessel to 70° C. until all are melted. At this point, the three ingredients are mixed until uniform. ACH is then stirred into the mixture with high speed mixing until uniform afterward, the microsphere FN510 are stirred into the mixture, high speed mixing again occurs to achieve uniform dispersion. The resulting uniform mixture is cooled to 55°-60° C., the product is then poured into stick mold containers and cooled.

The resultant anhydrous antiperspirant stick compositions rub off on the as a powder rather than as a gelled liquid. Other active antiperspirant chemical may used in lieu of ACH without any noticeable difference.

EXAMPLE 8

An anhydrous aerosol concentrate composition is made from the following:

|  | % |
| --- | --- |
| 1. Decamethyl cyclopentasiloxane (Pentamer) | 31.67 |
| 2. Microthene FN510 | 23.33 |
| 3. Aluminum chlorohydrate, standard powder (ACH) | 36.67 |
| 4. Bentone 38, (Hectorite clay) | 0.83 |
| 5. Isopropyl myristate (IPM) | 7.50 |

Isopropyl myristate and the Bentone 38 are added in a mixing vessel to the cyclomethicone. The three ingredients are mixed under a high speed stirring, after which time, the Bentone has expanded and the mixture is uniform. Then the ACH is stirred into the mixture at high speed, subsequent to which the microspheres FN510 are blended in at high speed mixing. The mixture is then homogenized. This concentrate is made into an aerosol fill by adding concentrate to propellent isobutane propellant in a ratio of 30% concentrate to 70% isobutane. The aerosol fill is then submitted for filling in pressurized containers.

The resulting aerosol antiperspirant delivers a dry powder upon application.

EXAMPLE 9

An insect repellent lotion is made from the following:

|   | % |
|---|---|
| 1. N,N-diethyl toluamide (DEET) | 40.00 |
| 2. SDA 40, ethyl alcohol | 15.00 |
| 3. Microthene FN510 | 45.00 |

The DEET and ethyl alcohol are mixed in a mixing vessel until uniform after which, the FN510 microspheres are added with high speed mixing to achieve uniform dispersion. The DEET is both a carrier and an active constituent. The resulting insect repellent lotion dries almost instantaneously when rubbed into the skin.

EXAMPLE 10

A sun protectant lotion is made from the following:

|   | % |
|---|---|
| 1. Mineral Oil, USP 200/210 SSU | 45.00 |
| 2. Octyl dimethyl PABA | 8.00 |
| 3. Benzophenone-3 | 3.00 |
| 4. Microthene FN510 | 44.00 |

The octyl dimethyl PABA and benzophenone-3 are heated together to 50° C. in a mixing vessel, at this point the mixture is clear. The mineral oil is then stirred into the mixture at medium speed stirring. Then the FN510 microspheres are added with high speed stirring to achieve uniform dispersion. The batch is cooled to room temperature and removed to a storage vessel. The resulting sunscreen lotion rubs into the skin immediately without stickiness, yet is completely dry to the touch and water resistant.

EXAMPLE 11

Skin Bleaching Lotion

|   | % |
|---|---|
| 1. Hydroquinone USP | 2.00 |
| 2. Caprylic triglyceride (med. chain triglyceride) | 53.00 |
| 3. Microthene FN 510 | 45.00 |
|   | 100.00% |

Heat the hydroquinone and medium chain triglyceride to 70° C. Cool to 50° C. and stir in the FN 510 with high speed mixing.

The skin bleaching lotion rubs into the skin without any sign of greasiness.

EXAMPLE 12

Glycerin Hand Lotion

|   | % |
|---|---|
| 1. Glycerin | 48.00 |
| 2. SD 40, ethyl alcohol | 17.00 |
| 3. Microthene FN510 | 35.00 |
|   | 100.00% |

Mix the glycerin and ethyl alcohol until uniform. Mix in the Microthene FN510 with high speed, stirring until a uniform dispersion is achieved.

The glycerin lotion rubs into the skin without any feeling of stickiness and dries almost instantly to give a smooth feel.

We claim:

1. A liquid or semisolid anhydrous composition suitable for topical application, comprising an inactive carrier consisting essentially of:
   a) 10-80% by weight of an anhydrous pharmaceutically accepted topically applicable carrier composition which is liquid or semi-solid at room temperature; and
   b) 15-50% by weight of polyolefin microspherical particles having an average diameter of less than 25 microns and having a density of greater than 0.915 g/ml, where the amount of microspherical particles constitutes at least 30% by weight of the said anhydrous pharmaceutically acceptable carrier; and further
   5 to 50% by weight of the total composition of an antiperspirant compound.

2. A composition according to claim 1 formulated as a roll-on antiperspirant, comprising 5-40% of an antiperspirant compound.

3. A composition of claim 1 in the form of an anhydrous antiperspirant comprising by weight:
   a) 20 to 50% of cyclomethicone
   b) 1 to 10% polyoxypropylene-15-stearyl ether
   c) 5 to 20% stearyl alcohol
   d) 5 to 50% polyolefin microspherical particles
   e) 10 to 30% antiperspirant compound
   to a total of 100%.

4. A composition according to claim 1 in the form of an anhydrous antiperspirant aerosol concentrate comprising:
   a) 15-50% cyclomethicone
   b) 1-20% isopropyl myristate
   c) 15-40% polyolefin microspherical particles
   d) 10-40% antiperspirant compound
   to a total of 100%.

5. A composition according to claim 1 in the form of an anhydrous antiperspirant cream composition comprising:
   a) 30-50% cyclomethicone
   b) 1-10% polyoxypropylene 14 butyl ether
   c) 15-40% polyolefin microspherical particles
   d) 10-30% antiperspirant compound
   to a total of 100%.

* * * * *